United States Patent [19]
Watanabe et al.

[11] Patent Number: 5,225,350
[45] Date of Patent: Jul. 6, 1993

[54] PARTICLE AGGLUTINATION PATTERN JUDGMENT METHOD

[75] Inventors: Haruhisa Watanabe, Hachioji; Satoshi Tanaka, Hino; Shinya Matuyama, Hachioji, all of Japan

[73] Assignee: Olympus Optical Co., Ltd., Tokyo, Japan

[21] Appl. No.: 941,752

[22] Filed: Sep. 3, 1992

Related U.S. Application Data

[63] Continuation of Ser. No. 566,149, Aug. 10, 1990, abandoned.

[30] Foreign Application Priority Data

Aug. 17, 1989 [JP] Japan .................. 1-212004
Aug. 17, 1989 [JP] Japan .................. 1-212005
Aug. 17, 1989 [JP] Japan .................. 1-212006

[51] Int. Cl.⁵ .......................... G01N 33/86
[52] U.S. Cl. ...................... 436/165; 436/43; 436/69; 436/518; 422/73; 364/413.08; 364/555; 356/39; 356/434; 356/441; 356/246; 352/6; 73/61.69
[58] Field of Search ........ 436/43, 34, 63, 69, 436/164, 165, 518, 805, 519, 520, 533, 534, 807, 808; 422/73; 364/413.08, 416, 555; 356/39, 434, 441, 246; 352/6; 23/61.69

[56] References Cited

U.S. PATENT DOCUMENTS

| | | | |
|---|---|---|---|
| 4,727,033 | 2/1988 | Hijikata et al. | 436/69 |
| 4,794,450 | 12/1988 | Saito et al. | 358/93 |
| 4,873,633 | 10/1989 | Louis et al. | 364/413.08 |

FOREIGN PATENT DOCUMENTS

| | | |
|---|---|---|
| 0046430A1 | 2/1982 | European Pat. Off. |
| 58-105065 | 6/1983 | Japan . |
| 61-215948 | 9/1986 | Japan . |
| 62-105031 | 5/1987 | Japan . |
| 63-58237 | 3/1988 | Japan . |

Primary Examiner—James C. Housel
Assistant Examiner—David Redding
Attorney, Agent, or Firm—Frishauf, Holtz, Goodman & Wodward

[57] ABSTRACT

Particle pattern images of the sample are optically measured by an image reader of a particle agglutination pattern judgment apparatus, and the measured particle pattern images are retrieved by a data processing controller to be able to execute pattern judgment processing. The data processing controller obtains predetermined parameters on the basis of the particle pattern images read by the image reader, and automatically judges an agglutination, non-agglutination, or unidentified attribute of each particle pattern on the basis of the obtained parameters. An operator visually observes the particle pattern images of the sample to visually determine an agglutination, non-agglutination, or unidentified attribute of each particle pattern of the sample. The operator inputs the visual judgment results in the particle agglutination pattern judgment apparatus using an input unit. The data processing controller changes at least one of the automatic judgment results and a threshold value according to the input visual judgment results.

11 Claims, 11 Drawing Sheets

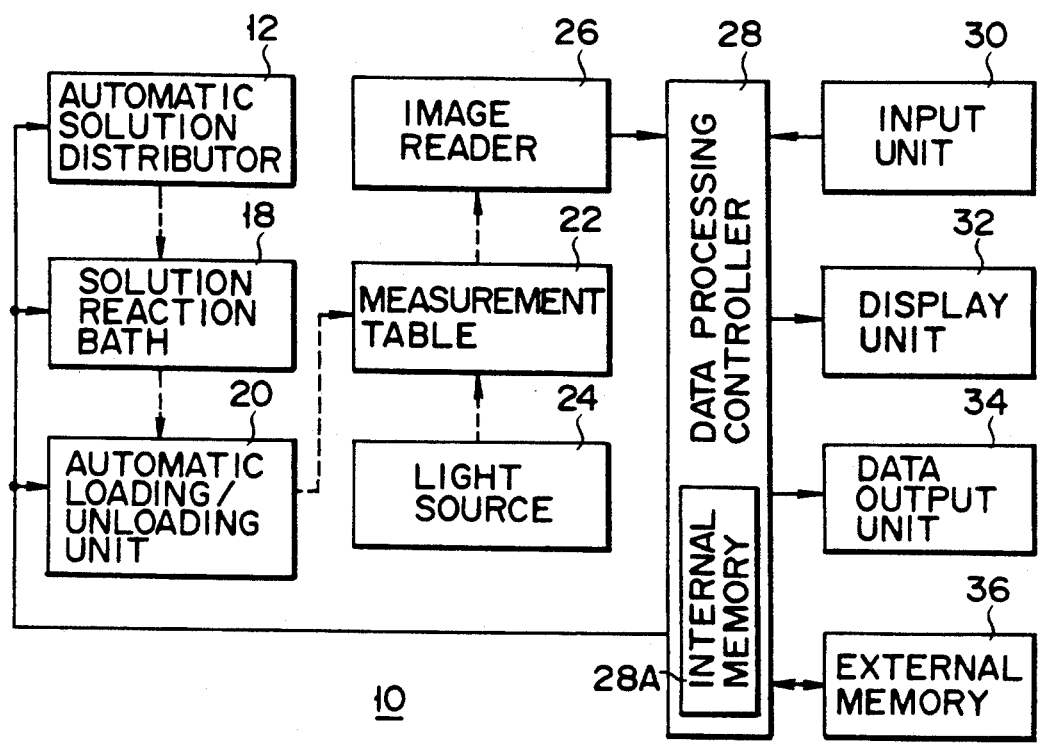
F I G. 1
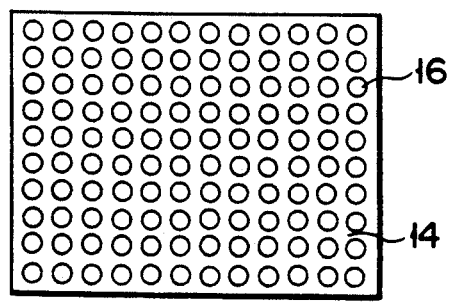
F I G. 2

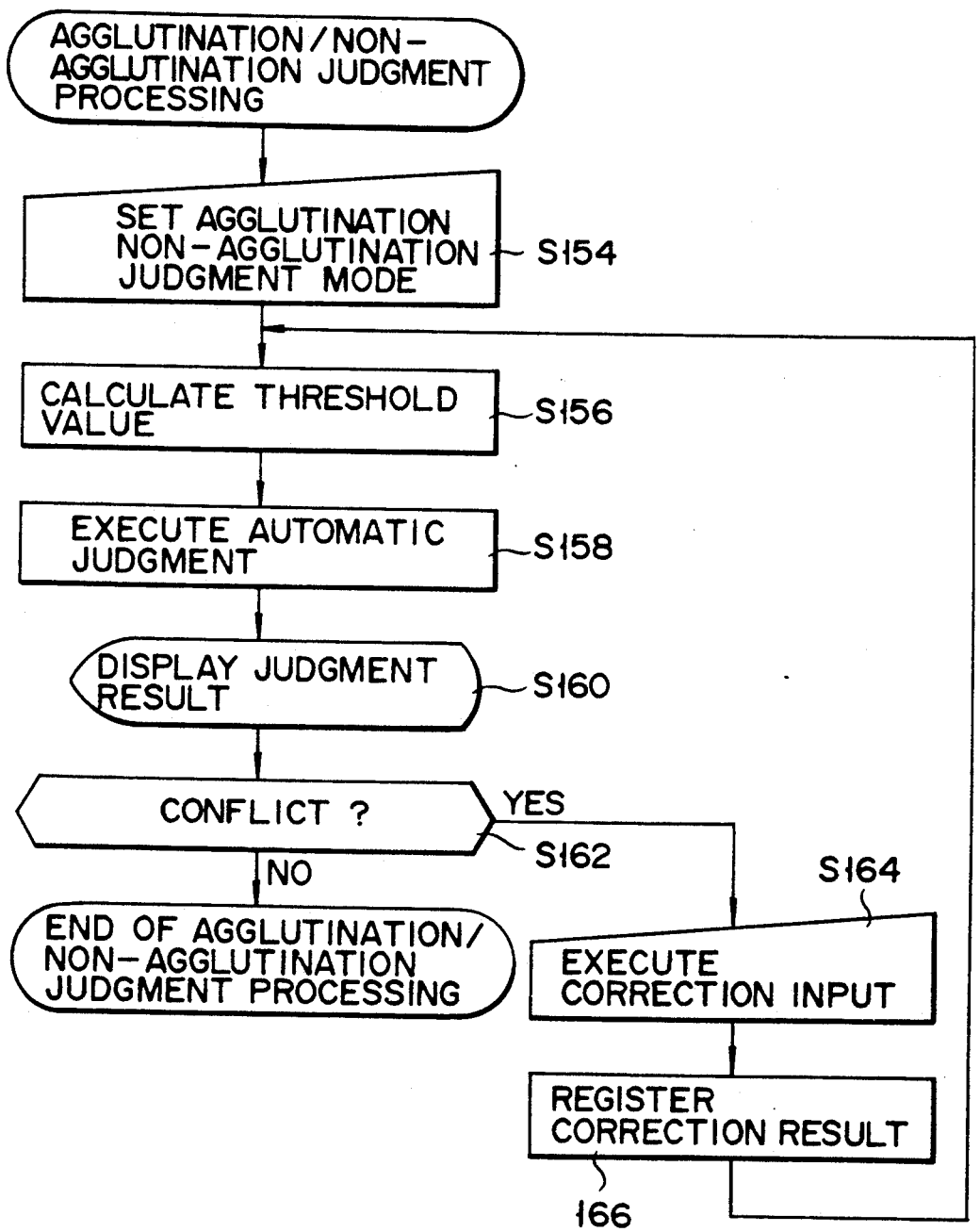
F I G. 3E

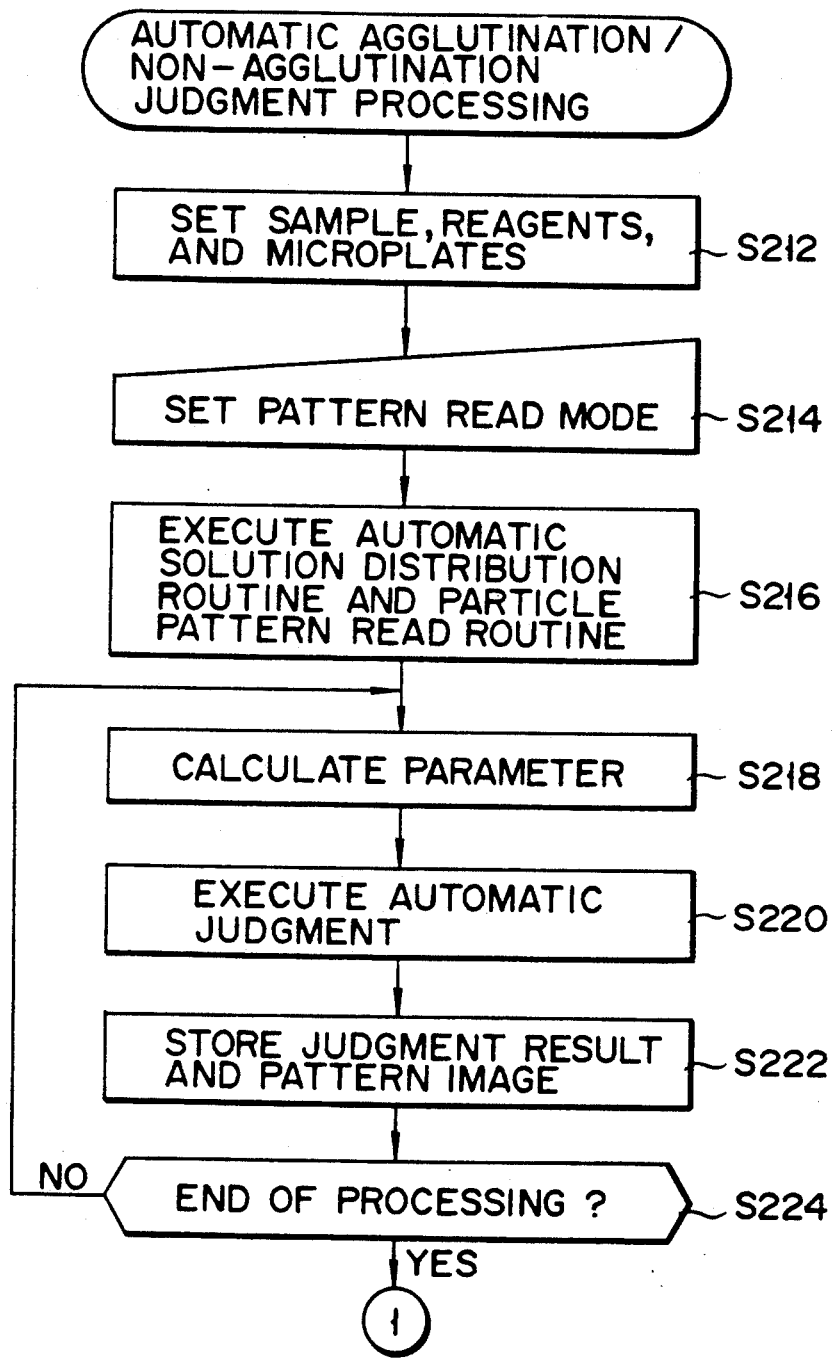
F I G. 4A

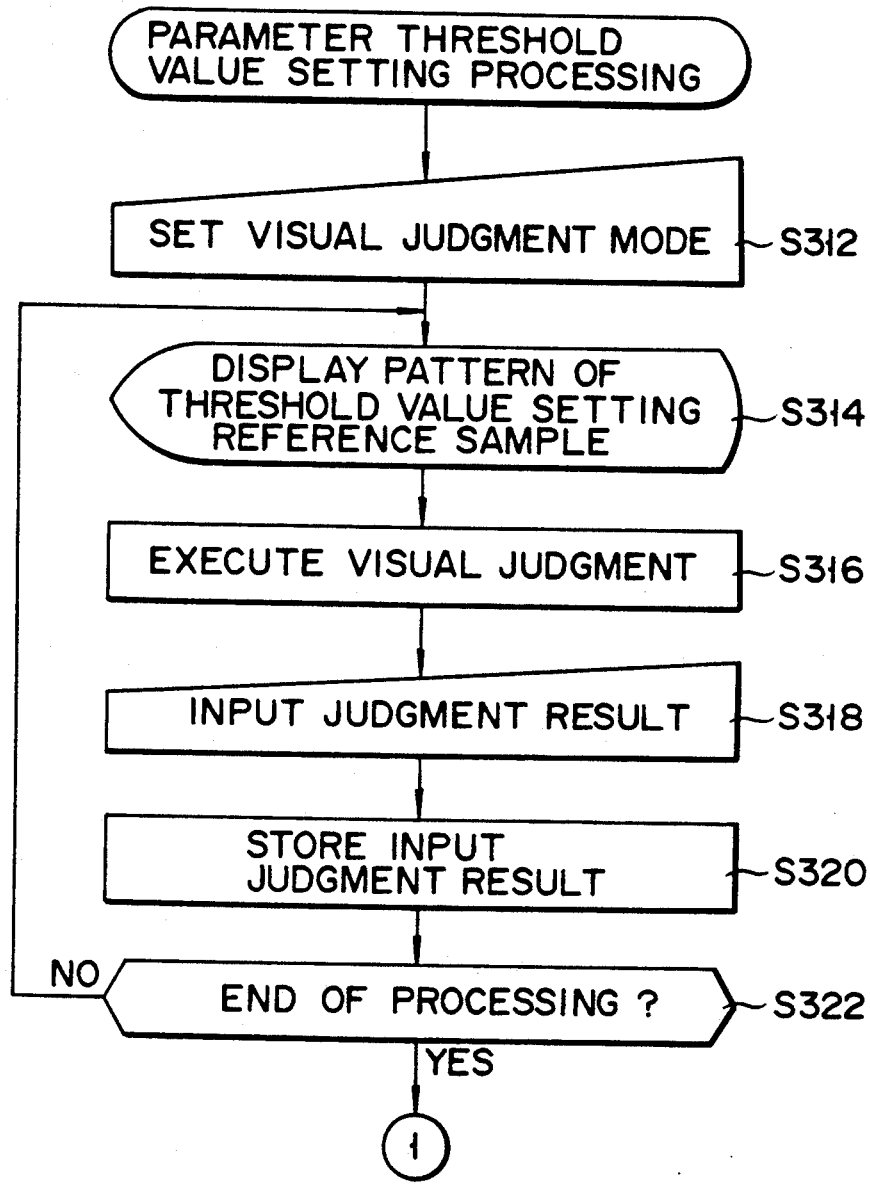
F I G. 6A

PARTICLE AGGLUTINATION PATTERN JUDGMENT METHOD

This application is a continuation of application Ser. No. 07/566,149, filed Aug. 10, 1990, now abandoned.

BACKGROUND OF THE INVENTION

1. Field of the Invention

The present invention relates to a particle agglutination pattern judgment method for optically measuring patterns of particles in sample solutions and automatically classifying attributes of patterns into agglutination, non-agglutination, and others.

2. Description of the Related Art

A conventional particle agglutination pattern judgment apparatus for judging agglutination, non-agglutination, and other patterns of particles in solutions is known, as disclosed in U.S. Pat. No. 4,727,033. The particle agglutination pattern judgment apparatus optically measures particle patterns, obtains parameters for attribute judgment, and compares the parameters with a predetermined threshold value to judge criteria to which attributes of the patterns belong.

In the particle agglutination pattern judgment apparatus, an unidentified pattern whose attribute cannot be automatically classified to agglutination/non-agglutination patterns tends to be found in the following cases:

(1) when particles themselves in a sample solution are abnormal (hemolysis of blood cells, abnormality of a particulate reagent, and the like);

(2) when a reagent which reacts with particles in a sample solution or a sample (e.g., an anti-A serum against a blood reagent, an anti-B serum reagent, a serum against a blood cell reagent, blood plasma, and the like) is abnormal, and a correct pattern cannot be formed;

(3) when a foreign matter is mixed in a sample solution;

(4) when a predetermined threshold value for executing automatic agglutination/non-agglutination judgment is not set to be a correct value for any reasons;

(5) when an operator at the particle agglutination pattern judgment apparatus gives priority to a visual judgment mode, and sets a threshold value which causes an automatic judgment result near a boundary of agglutination/non-agglutination patterns to indicate an unidentified pattern;

(6) when an original pattern cannot be formed due to, e.g., activation of a complement;

(7) when a microplate or the like is damaged; and (8) when the apparatus or the like causes an error.

When an unidentified pattern is generated in the above cases, an operator at the particle agglutination pattern judgment apparatus reexamines a sample which is determined as the unidentified pattern by visual observation using a visual judgment unit of the particle agglutination pattern judgment apparatus or a technique therefor, and corrects output data from a printer of the particle agglutination pattern judgment apparatus based on the visual judgment result. However, when the operator corrects data based on the visual judgment result, the following problems are (1) The operator must visually find a sample determined as an unidentified pattern by the particle agglutination pattern judgment apparatus, resulting in cumbersome operation.

(2) There is a time difference between when automatic judgment is performed in the particle agglutination pattern judgment apparatus and when the operator performs visual judgment, and the reason why the particle agglutination pattern judgment apparatus judges an unidentified pattern cannot be accurately recognized. More specifically, if there is a time difference, a pattern may be changed over time.

(3) Automatic judgment by the particle agglutination pattern judgment apparatus and visual judgment by the operator may often have different physical factors such as a vibration which changes a pattern. For this reason, the reason why the particle agglutination pattern judgment apparatus judges an unidentified pattern cannot often be accurately recognized.

(4) In any case, a judgment result correction operation requires cumbersome operations to search data of a sample which is determined as an unidentified pattern by the pattern judgment apparatus from printer output data, to visually rejudge a corresponding well of a microplate, and correct the result with a red pen.

These problems become serious especially in the large-scale particle agglutination pattern judgment apparatus having a high processing speed, thus causing artificial and other errors.

The predetermined threshold value must be properly set depending on differences in conditions to be described below, and must be changed depending on them:

(1) kinds of particles in a sample solution;

(2) a density of particles in a sample solution;

(3) kinds and a density of a reagent which reacts with particles or a sample; and (4) judgment reference of an operator who operates the particle agglutination pattern judgment apparatus.

In general, an operator inputs a threshold value determined based on these conditions in advance in the particle agglutination pattern judgment apparatus using an input unit such as a keyboard.

However, a method of judging attributes of patterns using the particle agglutination pattern judgment apparatus adopting such a threshold value setting method has the following problems:

(1) A threshold value is obtained by numerically expressing a predetermined portion of an agglutination pattern. It is difficult to associate the numerical value with a particle pattern, and it is cumbersome to determine a threshold value.

(2) In particular, when a plurality of threshold values are set and are associated with each other, it is very difficult to determine a proper value.

(3) Even if a threshold value is input as described above, the input value must be corrected and adjusted by try & error judgment experiments, and much time is required for setting a threshold value.

(4) An input operation at a keyboard or the like is troublesome for an operator who is not accustomed to the keyboard, and this may cause an operation error.

SUMMARY OF THE INVENTION

It is an object of the present invention to provide a particle agglutination pattern judgment method wherein a visual judgment result is fed back to a particle agglutination pattern judgment apparatus to facilitate rejudgment and edit operations of an unidentified pattern, or setting and correction operations of a threshold value.

More specifically, according to the present invention, there is provided a particle agglutination judgment method for automatically classifying attributes of particle patterns of a sample into agglutination, non-agglutination, and other attributes, comprising the steps of preparing a particle agglutination pattern judgment apparatus comprising reading means for optically measuring particle pattern images of the sample, and reading the particle pattern images to be able to execute pattern judgment processing, parameter calculation means for obtaining predetermined parameters on the basis of the particle pattern images read by the reading means, judgment means for automatically judging an agglutination, non-agglutination, or unidentified attribute of each particle pattern of the sample on the basis of the parameters calculated by the parameter calculation means and a threshold value of the parameter as a judgment reference, and input means for manually inputting data, causing the reading means of the particle agglutination pattern judgment apparatus to optically measure the particle pattern images of the sample and to read the particle pattern images to be able to execute the pattern judgment processing, causing the parameter calculation means of the particle agglutination pattern judgment apparatus to obtain the predetermined parameters on the basis of the particle pattern images read by the reading means, automatically judging an agglutination, non-agglutination, or unidentified attribute of each particle pattern of the sample on the basis of the parameters calculated by the parameter calculation means by the judgment means of the particle agglutination pattern judgment apparatus, visually observing the particle pattern images of the sample to visually judge an agglutination, non-agglutination, or unidentified attribute of each particle pattern of the sample and obtain visual judgment results, inputting the visual judgment results of the visually observing step to the particle agglutination pattern judgment apparatus using the input means of the particle agglutination pattern judgment apparatus, and changing at least one of (A) the judgment results in the automatically judging step by the judgment means and (B) the judgment reference.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a block diagram of a particle agglutination pattern judgment apparatus used for carrying out a particle agglutination pattern judgment method according to the first embodiment of the present invention;

FIG. 2 is a plan view of a microplate;

FIGS. 3A to 3E are flow charts for explaining processing for determining a threshold value in the first embodiment;

FIGS. 4A to 4C are flow charts for explaining automatic agglutination/non-agglutination judgment processing in the first embodiment;

FIGS. 6A and 6B are flow charts for explaining processing for determining a threshold value in the second embodiment.

DETAILED DESCRIPTION OF THE PREFERRED EMBODIMENTS

Figure 3A:
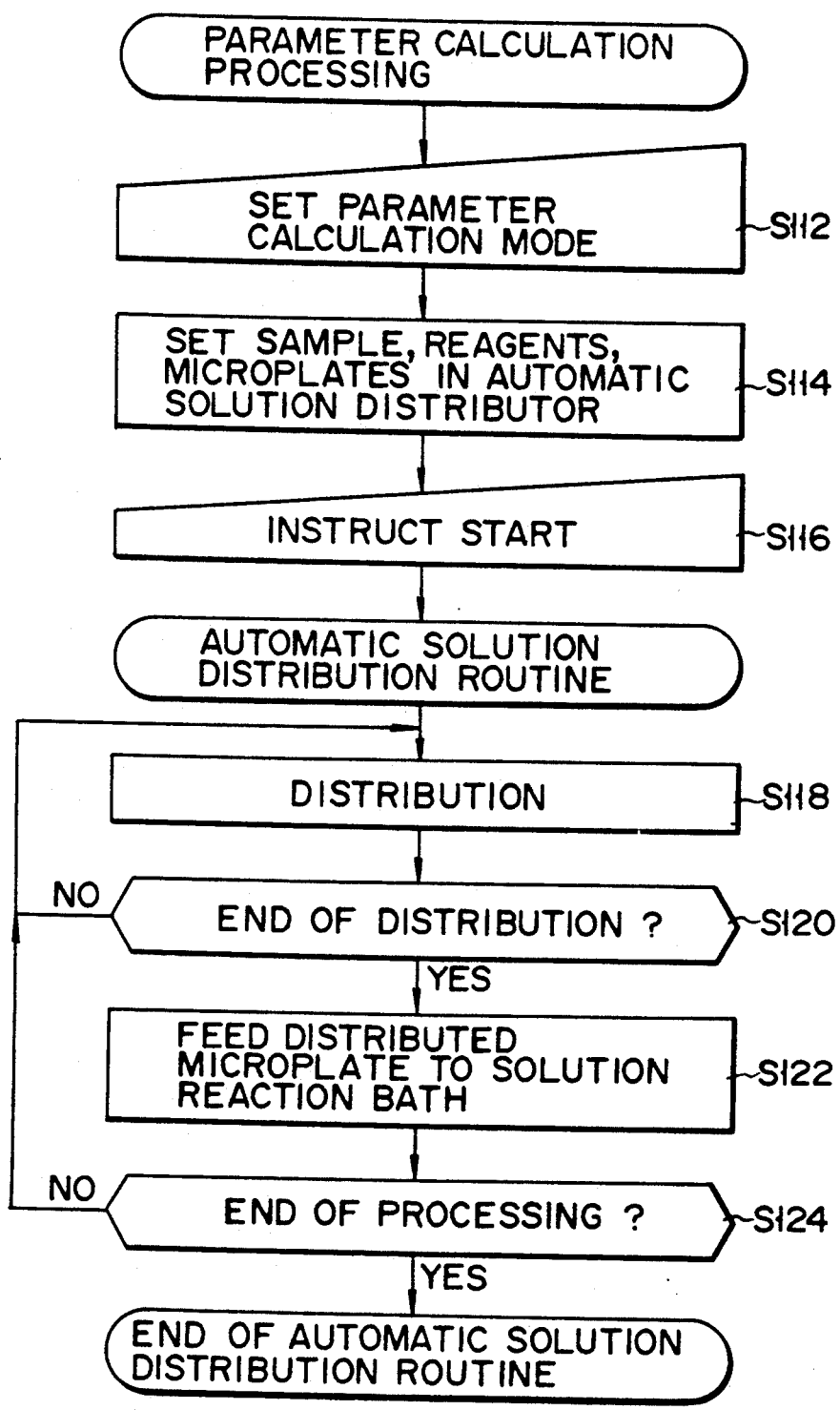

Prior to a description of a particle agglutination pattern judgment method according to the first embodiment of the present invention, a particle agglutination pattern judgment apparatus used for practicing this embodiment will be described below.

FIG. 1 is a block diagram of a particle agglutination pattern judgment apparatus 10. In FIG. 1, an automatic solution distributor 12 automatically distributes a sample and reagents in wells 16 of a microplate 14 shown in FIG. 2. A solution reaction bath 18 holds the microplate 14 for a predetermined period of time to react a sample solution distributed on the microplate 14 by the automatic solution distributor 12. An automatic loading/unloading unit 20 automatically sets the microplate 14 in the solution reaction bath 18 on a measurement table 22, and unloads it therefrom.

A light source 24 radiates light on the microplate 14 set on the measurement table 22. Light transmits through the wells 16 of the microplate 14 and the sample solution in each well 16, and is guided onto a particle pattern (or image) reader 26 which opposes the light source 24 to sandwich the measurement table 22 therebetween. The transmission light forms a particle pattern image of the sample solution in each well 16 of the microplate 14 on the image reader 26. The image reader 26 has a photoelectric conversion function, and an analog-to-digital (A/D) conversion function. Therefore, an optical image formed on the image reader 26 is converted into a digital electrical signal. The converted particle pattern image is supplied to a data processing controller 28.

The data processing controller 28 controls operasolution reaction bath 18, and the automatic loading/unloading unit 20. The controller 28 also processes the particle pattern image read by the image reader 26, and acquires and stores parameters of the particle pattern for agglutination/non-agglutination judgment. The parameter includes a ratio (P/C) of a transmittance (P) at its surrounding portion to a transmittance (C) at the central portion of each well 16 as disclosed in U.S. Pat. No. 4,727,033, and the like. The data processing controller 28 has an internal memory 28A for storing various data.

An input unit 30 includes a keyboard for inputting a control instruction and a visual judgment result to the data processing controller 28. A display unit 32 includes a CRT or the like for displaying a read particle pattern image, output data and the like calculated by the data processing controller 28, and instructions for the operator. A data output unit 34 includes a printer for recordinq and outputting the output data and the like. An external memory 36 stores a read pattern image, the output data, and the like.

A threshold value for agglutination/non-agglutination judgment is determined using the particle agglutination pattern judgment apparatus 10 with the above arrangement in a sequence as shown in the flow charts of FIGS. 3A to 3E.

First, parameter calculation processing is executed. More specifically, an operator sets the particle agglutination pattern judgment apparatus 10 in a "parameter calculation mode" using the input unit 30 (step S112), as shown in FIG. 3A. Then, the operator sets a given sample, a plurality of reagents, and a predetermined number of microplates 14 in the automatic solution distributor 12 (step S114), and starts the pattern judgment apparatus 10 using the input unit 30 (step S116).

The particle agglutination pattern judgment apparatus 10 executes an automatic solution distribution routine according to a start instruction from the input unit 30. More specifically, the data processing controller 28 operates the automatic solution distributor 12 to automatically distribute the sample and the reagents on the wells 16 of each microplate 14 (step S118). Upon completion of distribution on all the wells of a given microplate 14 (step S120), this microplate 14 is fed to the solution reaction bath 18, and the automatic solution distributor 12 executes automatic distribution for the wells 16 of the next microplate 14 (step S122). When automatic distribution for all the predetermined number of microplates 14 set in the automatic solution distributor 12 is completed (step S124), the automatic solution distribution routine is ended.

Figure 3B:
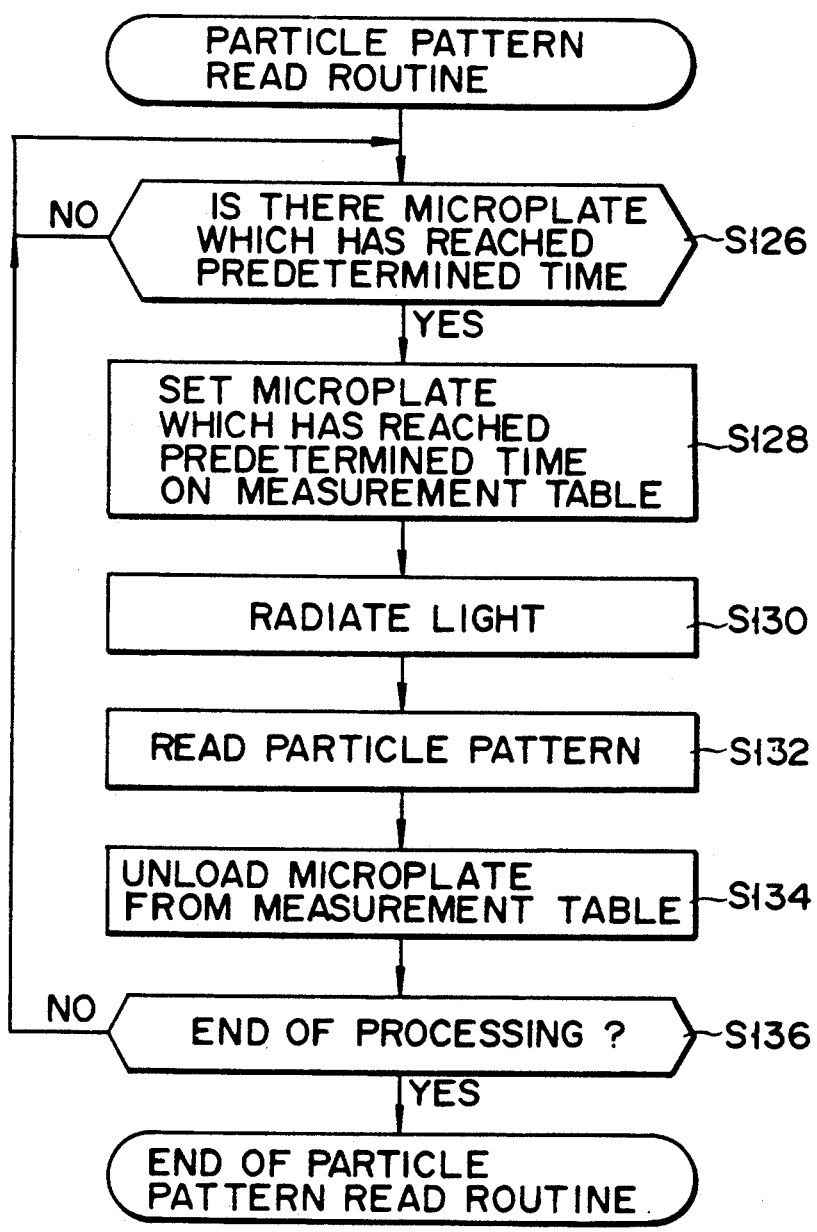

Parallel to some steps of the automatic solution distribution routine, the particle agglutination pattern judgment apparatus 10 executes a particle pattern read routine, as shown in FIG. 3B. More specifically, if it is determined in step S126 that at least one of the microplates 14 sequentially fed to the solution reaction bath 18 has been subjected to a reaction treatment for a predetermined period time, the corresponding microplate 14 is set on the measurement table 22 by the automatic loading/unloading apparatus 20 (step S128). Light emitted from the light source 24 is radiated on each well 16 of the microplate 14 set on the measurement table 22 (step S130), and pattern images defined by the light transmitting therethrough are formed on the image reader 26. The image reader 26 converts each pattern image into digital image data, and sends it to the data processing controller 28 (step S132). The microplate 14 whose pattern images are read are unloaded from the measurement table 22 by the automatic loading/unloading unit 20 (step S134). If reading of particle patterns of all the wells 16 of the predetermined number of microplates 14 is completed (step S136), the particle pattern read routine is ended.

Figure 3C:
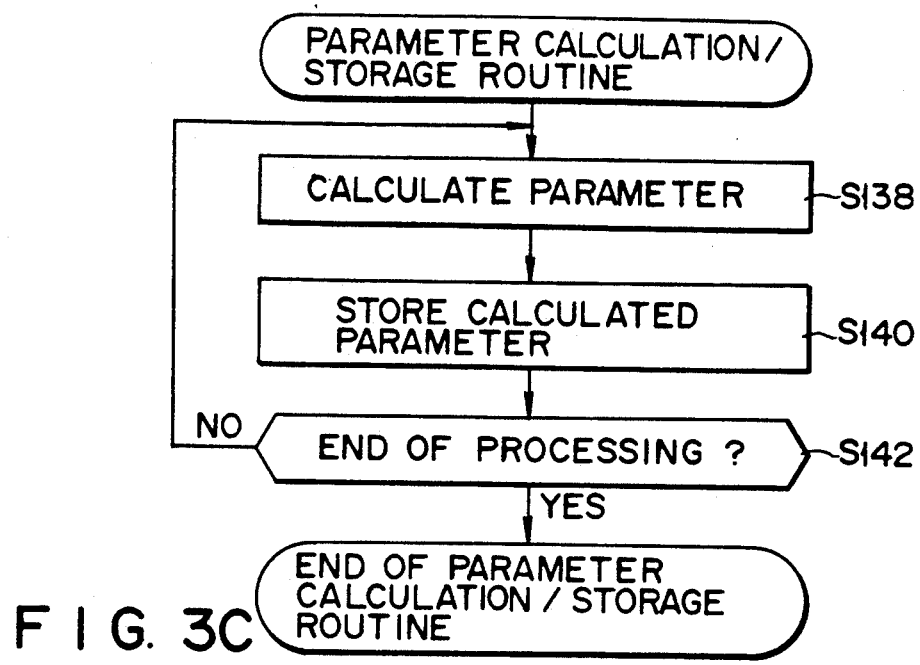

Parallel to some steps of the particle pattern read routine, a parameter calculation/storage routine is executed, as shown in FIG. 3C. More specifically, the data processing controller 28 executes image processing of image data of each particle pattern supplied from the image reader 26 in step S132, and calculates a parameter for agglutination/non-agglutination judgment (step S138). As the parameter, for example, a transmittance (P/C) calculated based on a transmittance (C) of the central portion of each well 16 and a transmittance (P) of its surrounding portion is utilized. The data processing controller 28 stores the calculated parameter in the internal memory 28A (step S140). Upon completion of calculations and storage of parameters for the wells 16 of all the microplates 14 (step S142), the parameter calculation/storage processing is ended, and the parameter calculation processing is ended.

Figure 3D:
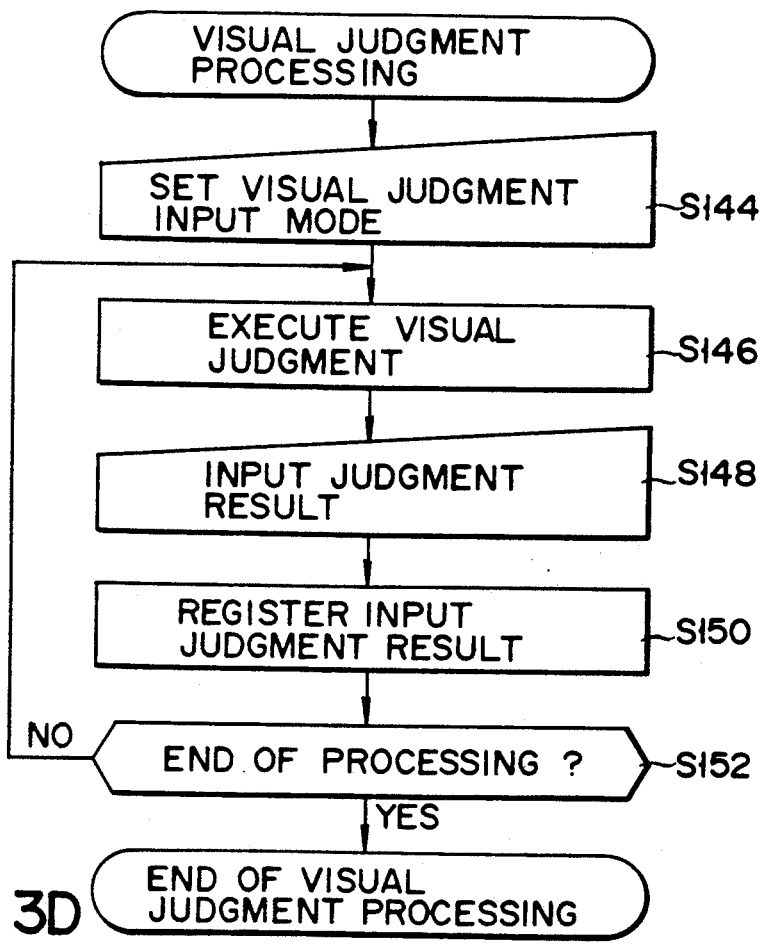

As described above, when the parameter calculation processing is ended, visual judgment processing shown in FIG. 3D is executed. More specifically, the operator sets the particle agglutination pattern judgment apparatus 10 in a "visual judgment input mode" using the input unit 30 (step S144). The operator visually judges agglutination/non-agglutination states of the patterns of all the samples on the wells 16 of the microplates 14 for which the parameters are calculated in the parameter calculation/storage routine (step S146). The operator inputs the judgment results from the input unit 30 (step S148), and registers them in the internal memory 28A of the data processing controller 28 (step S150). In this manner, after the visual judgment results of all the samples on the wells 16 of all the microplates 14 are registered (step S152), the visual judgment processing is ended.

Upon completion of the visual judgment processing, agglutination/non-agglutination judgment processing shown in FIG. 3E is then executed. More specifically, the operator switches the particle agglutination pattern judgment apparatus 10 to an "agglutination/non-agglutination judgment mode" using the input unit 30 (step S154). The data processing controller 28 looks up the internal memory 28A compares the parameters for all the samples stored in step S140 and the visual judgment results registered in step S150 to calculate a threshold value of the parameter which least conflicts with the corresponding visual judgment result, and stores the result in the internal memory 28A (step S156). The data processing controller 28 automatically judges agglutination/non-agglutination states of the parameters of all the samples stored in the internal memory 28A using the calculated threshold value (step S158). The controller 28 then displays the automatic judgment results on the display unit 32 (step S160).

The operator checks based on the output data displayed on the display unit 32 if there are conflicts between the visual judgment results registered by himself or herself and the automatic judgment results of the particle agglutination pattern judgment apparatus 10. If the number of conflicts is larger than, e.g., an allowable number (step S162), the operator performs correction for reregistration using the input unit 30 (step S164). The data processing controller 28 reregisters the visual judgment results in the internal memory 28A according to the correction operation (step S166), and then repeats processing from step S156.

In this manner, when the processing and operations in steps S156 to S166 are repeated several times, a proper threshold value can be determined.

Figure 4B:
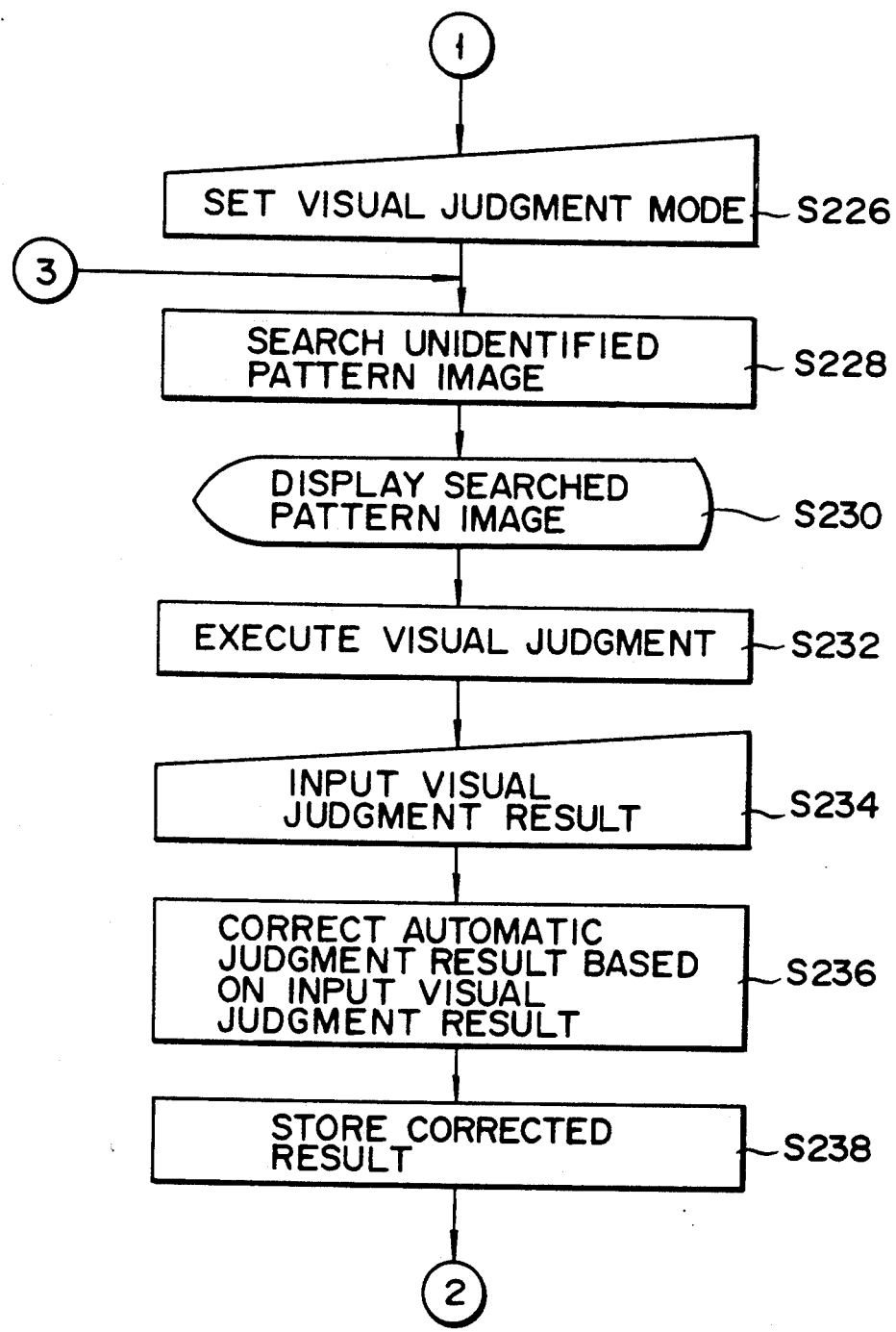
Figure 4C:
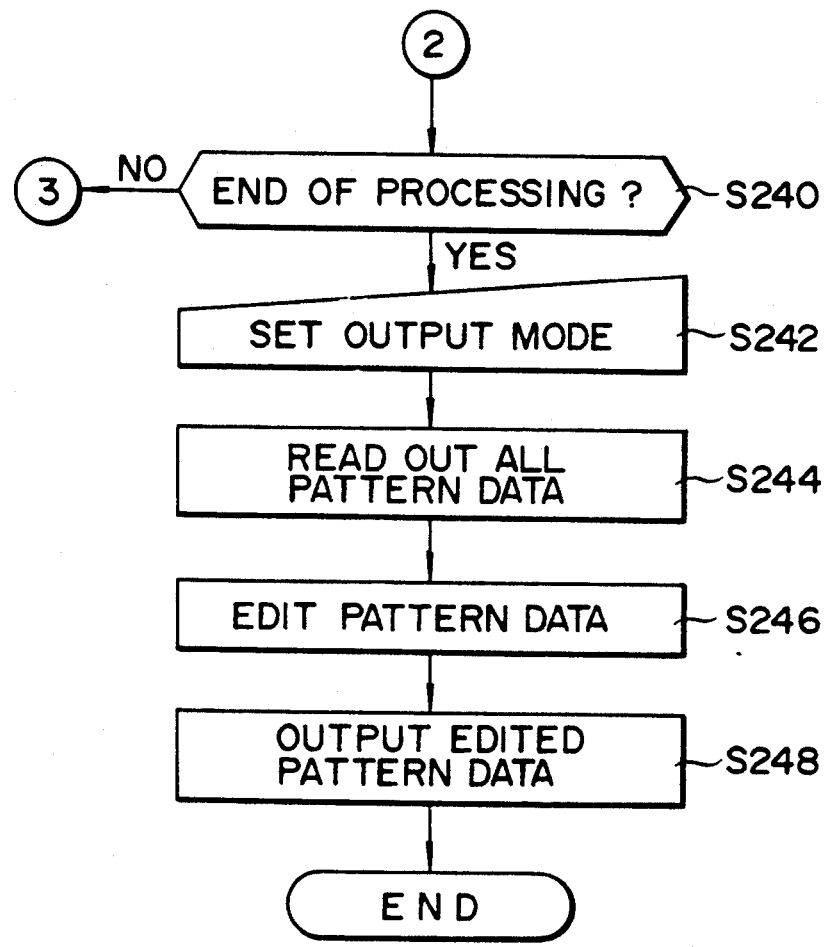

When the proper threshold value is determined in this manner, automatic agglutination/non-agglutination judgment is then executed in a sequence shown in FIGS. 4A to 4C.

For example, the operator replaces the sample with another one, and sets reagents and another plurality of microplates 14 in the automatic solution distributor 12 (step S212). The operator then sets the particle agglutination pattern judgment apparatus 10 in the "pattern read mode" using the input unit 30 (step S214). The particle agglutination pattern judgment apparatus 10 executes the automatic solution distribution routine, and the particle pattern read routine as described above (step S216). The data processing controller 28 executes image processing of image data of particle patterns supplied from the image reader 26, and calculates parameters for agglutination/non-agglutination judgment (step S218). The controller 28 then automatically judges based on the calculated parameters and the threshold value determined as described above whether or not a certain particle pattern is an agglutination pattern, a non-agglutination pattern, or an unidentified pattern which cannot be judged to belong to one of the former two patterns, and classifies the patterns (step S220). The controller 28 stores the automatic judgment results in the external memory 36 in correspondence with the pattern images (step S222). Steps S218 to S222 are repeated until all the samples are automatically judged (step S224).

When the automatic judgment results and pattern images of all the samples are stored, the operator sets the particle agglutination pattern judgment apparatus 10 in the "visual judgment mode" using the input unit 30 (step S226). In the visual judgment mode, pattern images whose automatic judgment results indicate unidentified patterns are searched from those stored in the external memory 36 in step S222 (step S228), and the searched patterns are displayed on the display unit 32 (step S230). The operator visually judges the unidentified pattern images to classify them into agglutination, non-agglutination, or other patterns (step S232), and inputs the visual judgment results in the data processing controller 28 using the input unit 30 (step S234). The data processing controller 28 corrects the automatic judgment results according to the input visual judgment results (step S236), and stores them in the external memory 36 (step S238). The processing from step S228 is repeated until all the unidentified patterns are corrected and stored (step S240).

The operator then sets the particle agglutination pattern judgment apparatus 10 in an "output mode" using the input unit 30 (step S242). When the output mode is set, the data processing controller 28 reads out all the pattern data including data corrected and stored in steps S236 and S238 from the external memory 36 (step S244), edits these data in a predetermined format (step S246), and outputs them using the data output unit 34 (step S248).

When the threshold value is determined with the above-mentioned sequence, the following effects can be expected:

(1) The operator of the pattern judgment need only visually judge particle patterns and register the judgment results regardless of a numerically expressed threshold value. Thus, a threshold value can be determined by a simple operation, and agglutination/non-agglutination judgment can be facilitated.

(2) Even when a threshold value must be finely adjusted, try & error judgment experiments are not necessary unlike in a conventional method, and a threshold value can be determined within a short period of time.

(3) When there are a large number of samples, a predetermined number of samples are randomly selected from a mother group of all the samples, a threshold value is determined on the basis of the predetermined number of samples, and agglutination/non-agglutination judgment of particle patterns of all the samples can be executed using the determined threshold value. As a result, operations can be greatly facilitated, and a judgment time can also be shortened.

When the automatic agglutination/non-agglutination judgment is performed with the above-mentioned sequence, the following effects can be expected:

(1) Since an unidentified pattern which is classified to neither the agglutination nor non-agglutination patterns can be automatically displayed with a simple operation, no cumbersome operations for visual judgment are required, and an artificial error hardly occurs.

(2) An input operation of visual judgment result is also easy, and does not require cumbersome operations as compared to a conventional method.

(3) Since a displayed unidentified pattern is visually observed and judged, and a judgment result is input at that time, erroneous registration and edit operations of a wrong pattern can be prevented.

(4) Since a pattern image when automatic judgment by the apparatus is displayed, a pattern image which is free from a change in pattern due to a time difference or a vibration can be visually reexamined, a cause of judging an unidentified pattern can be accurately pursued.

Figure 5:
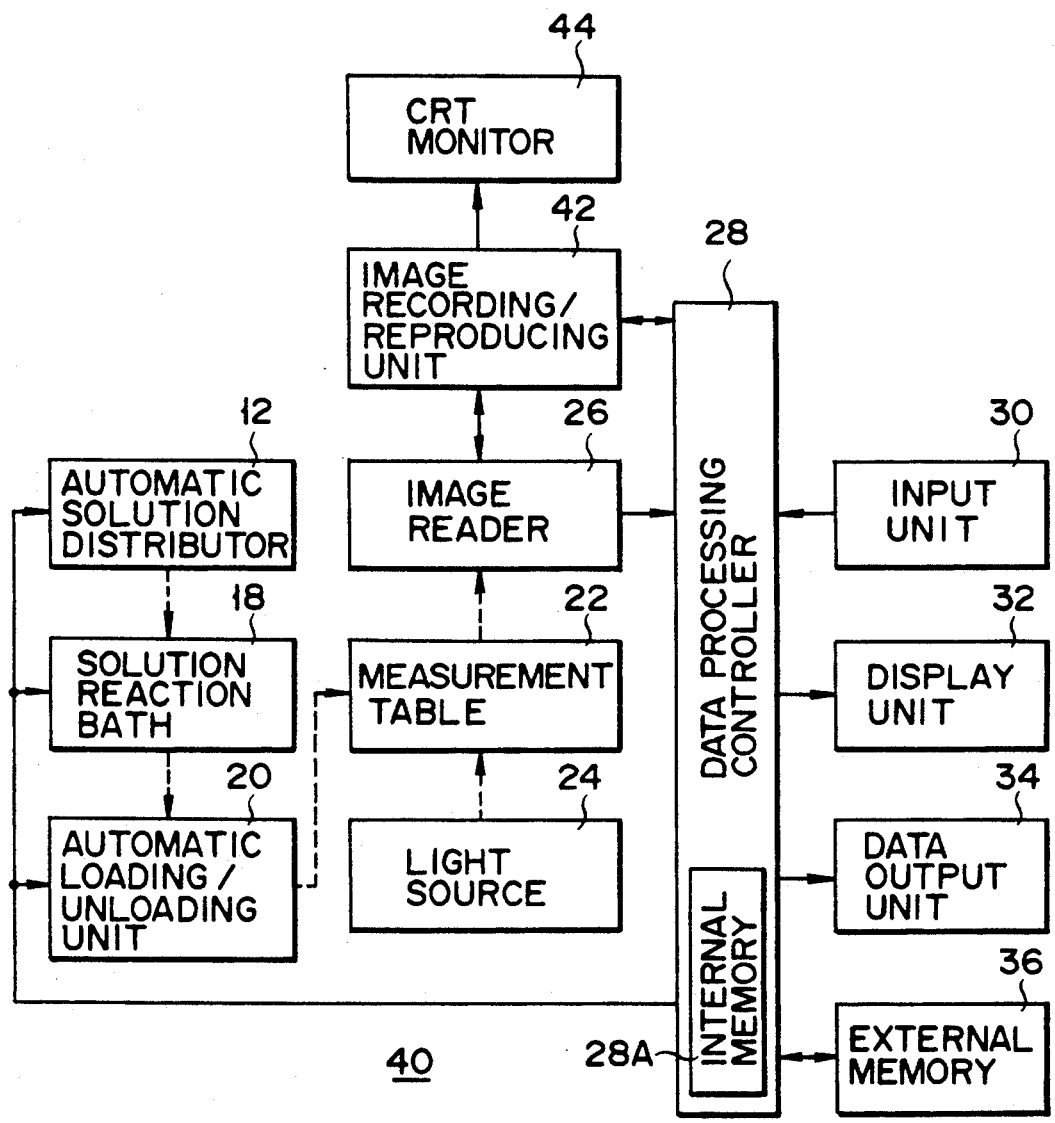
FIG. 5 is a block diagram of a particle agglutination pattern judgment apparatus used for carrying out a particle agglutination pattern judgment method according to the second embodiment of the present invention.

FIG. 5 is a particle agglutination pattern judgment apparatus 40 used for practicing a particle agglutination pattern judgment method according to the second embodiment of the present invention. The same reference numerals in FIG. 5 denote the same parts as in FIG. 1, and a detailed description thereof will be omitted. More specifically, in this particle agglutination pattern judgment apparatus 40, an image recording/reproducing unit 42 for recording/reproducing a plurality of patterns of threshold value setting reference samples, and a CRT monitor 44 for displaying a pattern of a threshold value setting reference sample recorded in the image recording/reproducing unit 42 are added to the pattern judgment apparatus 10 shown in FIG. 1. The image recording/reproducing unit 42 can comprise, e.g., a VTR or an optical disk apparatus.

Figure 6B:
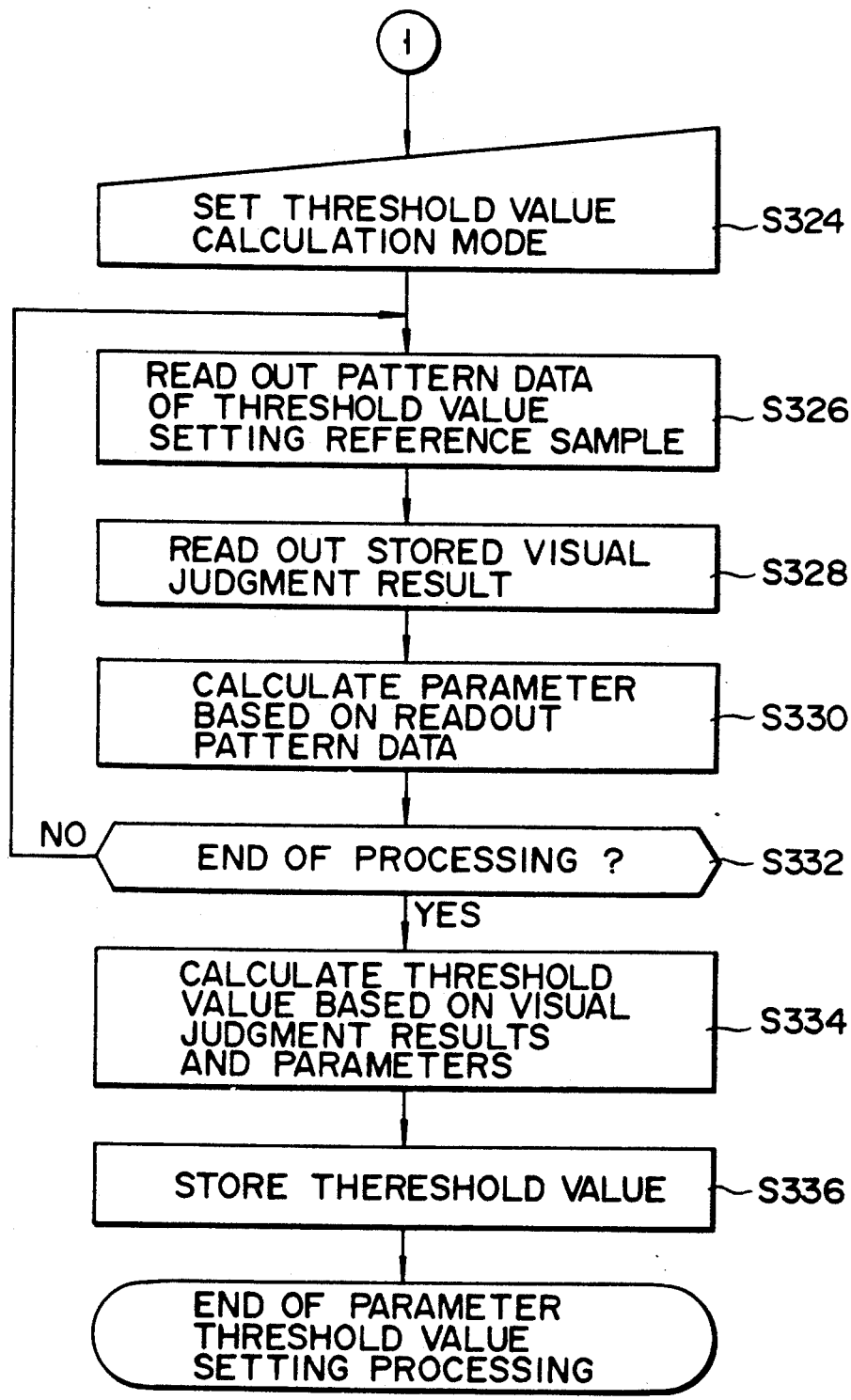

A threshold value for agglutination/non-agglutination judgment is determined using the particle agglutination pattern judgment apparatus 40 with the above arrangement in a sequence as shown in the flow charts of FIGS. 6A and 6B. In this embodiment, the threshold value is determined using a pattern of a threshold value setting reference sample recorded in advance in the image recording/reproducing unit 42.

More specifically, the operator sets the particle agglutination pattern judgment apparatus 40 in a "visual judgment mode" using the input unit 30 (step S312). The data processing controller 28 controls the image recording/reproducing unit 42 to display one of the threshold value setting reference samples which are recorded in advance in the image recording/reproducing unit 42 on the CRT monitor 44 (step S314). The operator visually observes the pattern of the threshold value setting reference sample displayed on the CRT monitor 44, and judges whether the displayed pattern is an agglutination or non-agglutination pattern (step S316). The operator then inputs the judgment result to the data processing controller 28 using the input unit 30 (step S318) The data processing controller 28 stores the input visual judgment result in the image recording/reproducing unit 42 in correspondence with the pattern of the threshold value setting reference sample (step S320). In this manner, steps S314 to S320 are repeated until visual judgment for all the threshold value setting reference samples recorded in advance in the image recording/reproducing unit 42 is completed (step S322).

Upon completion of the visual judgment operations, the operator sets the particle agglutination pattern judgment apparatus 40 in a threshold value calculation mode using the input unit 30 (step S324). The data processing controller 28 reads out pattern data of the threshold value setting reference sample from the image recording/reproducing unit 42 via the image reader 26 (step S326). At the same time, the visual judgment results stored in the image recording/reproducing unit 42 in step S320 are also read out, and are stored in the internal memory 28A (step S328). The parameter as described above for judging an agglutination/non-agglutination attribute of the reference sample is calculated on the basis of the pattern data of the threshold value setting reference sample read out in step S326, and is stored in the internal memory 28A (step S330). In this manner, steps S326 to S330 are repeated until the parameters are calculated for all the threshold value setting reference samples.

In this manner, when the parameters are calculated for all the threshold value setting reference samples, the data processing controller 28 reads out all the parameters and the corresponding visual judgment results stored in the internal memory 28A, and compares them to calculate a threshold value for the parameters (step S334). The calculated parameter is stored in the internal memory 28A as an initial setup value (step S336), and is used in judgment of an actual sample later.

Since judgment of an actual sample is the same as the automatic agglutination/non-agglutination judgment processing described above with reference to FIGS. 4A and 4B, a detailed description thereof will be omitted. In this case, automatic judgment in step S220 is executed using the threshold value stored in the internal memory 28A, as a matter of course.

When the threshold value is determined in the above-mentioned sequence, the following effects can be expected:

(1) The operator at the particle agglutination pattern judgment apparatus can initialize the particle agglutination pattern judgment apparatus with a simple operation giving priority to visual judgment regardless of a numeric threshold value.

(2) For this reason, setting errors can be minimized.

(3) Even when a threshold value must be finely adjusted, try & error judgment experiments are not necessary unlike in a conventional method.

(4) Since the threshold value can be easily and accurately set as described above, a large number of samples can be accurately processed within a short period of time in judgment of actual samples.

In the second embodiment, the threshold value determination sequence of the first embodiment described above is developed. More specifically, in the threshold value determination sequence of the first embodiment, it is difficult for an operator who is not accustomed to visual judgment of agglutination/non-agglutination states of sample patterns in wells of the microplate to properly discriminate a continuous change in patterns from an agglutination state to a non-agglutination state, and to judge agglutination/non-agglutination patterns, and is often confused of judgment. As a result, the number of samples which conflict with judgment results by the particle agglutination pattern judgment apparatus is increased, and much labor and time tend to be required to determine an optimal threshold value. In order to assist visual judgment, a reference sample in which patterns are continuously changed from an agglutination state to a non-agglutination state is prepared and stored, and is used to determine a threshold value. Thus, it is convenient for such an operator since he or she can make judgment while observing the reference sample, and a time required for judgment can be shortened.

However, when such a reference sample is formed using an actual sample, the sample suffers from a considerable change over time, and is not suitable for long-term preservation. When such a reference sample is formed based on an actual sample, it requires much labor and time. In the second embodiment, the formed reference sample is recorded in the image recording/reproducing unit and can be easily utilized by anyone to determine a threshold value. Therefore, the second embodiment has an advantage for an operator who is not accustomed to visual observation of an agglutination/non-agglutination state of sample patterns in wells of the microplate to simply and easily set a threshold value as compared to the first embodiment.

In the first embodiment, the order of the parameter calculation processing in steps S112 to S142 and the visual judgment/registration operations in steps S144 to S152 may be reversed. A control mechanism for the particle agglutination pattern judgment apparatus may be modified from those of the first embodiment, so that parameter calculation by the particle agglutination pattern judgment apparatus and visual judgment for a certain well 16 can be simultaneously executed. With this judgment method, there is no time difference between parameter calculation by the particle agglutination pattern judgment apparatus and visual judgment, and judgment precision can be improved. A parameter for agglutination/non-agglutination judgment may be selected as needed.

In step S222 in the automatic agglutination/non-agglutination judgment processing, both the judgment results and pattern images are stored. However, only unidentified patterns may be stored. A storage destination of these patterns is not limited to the external memory 36. For example, they may be stored in, e.g., an image recording/reproducing unit used in the second embodiment.

Visual judgment and threshold value calculation in the second embodiment may be executed simultaneously or in a reverse order.

Additional advantages and modifications will readily occur to those skilled in the art. Therefore, the invention in its broader aspects is not limited to the specific details, and illustrated examples shown and described herein. Accordingly, various modifications may be made without departing from the spirit or scope of the general inventive concept as defined by the appended claims and their equivalents.

What is claimed is:

1. A particle agglutination judgment method for automatically classifying attributes of particle patterns of a sample into agglutination, non-agglutination, and other attributes, comprising the steps of:

providing a particle agglutination pattern judgment apparatus comprising reading means for optically measuring particle pattern images of the sample, and reading the particle pattern images to be able to execute pattern judgment processing; parameter calculation means for calculating predetermined parameters on the basis of the particle pattern images read by said reading means; judgment means for automatically judging an agglutination, non-agglutination, or unidentified attribute of each particle pattern of the sample on the basis of the parameters calculated by said parameter calculation means and a threshold value of the parameter; input means for manually inputting data; display means for displaying the particle pattern images read by said reading means; and pattern image storage means for storing the particle pattern images read by said reading means and the judgment results by said judgment means;

causing said reading means of said particle agglutination pattern judgment apparatus to optically measure the particle pattern images of the sample and to read the particle pattern images to be able to execute the pattern judgment processing;

causing said parameter calculation means of said particle agglutination pattern judgment apparatus to calculate the predetermined parameters on the basis of the particle pattern images read by said reading means;

automatically judging an agglutination, non-agglutination, or unidentified attribute of each particle pattern of the sample on the basis of the parameters calculated by said parameter calculation means by said judgment means of said particle agglutination pattern judgment apparatus;

storing the judgment results, obtained when said judgment means automatically judges an agglutination, non-agglutination, or unidentified attribute of each particle pattern of the sample, in said pattern image storage means in correspondence with the particle pattern images;

displaying particle pattern images corresponding to the unidentified attribute of the automatic judgment results stored in said pattern image storage means by said display means;

visually observing the particle pattern images displayed on said display means to visually judge an agglutination, non-agglutination, or unidentified attribute of each particle pattern of the sample and obtain visual judgment results;

inputting the visual judgment results of the visually observing step to said particle agglutination pattern judgment apparatus using said input means of said particle agglutination pattern judgment apparatus; and changing the judgment results in the automatically judging step.

2. The method according to claim 1, further comprising a step of preparing rewriting means for changing a storage content of said pattern image storage means in said particle agglutination pattern judgment apparatus, and wherein the changing step includes a step of rewriting the automatic judgment results stored in said pattern image storage means with the input visual judgment results input by said input means.

3. The method according to claim 2, wherein the step of storing the judgment results in said pattern image storage means in correspondence with the particle patterns includes a step of storing the judgment result in correspondence with the particle pattern image only when an unidentified attribute is judged in the automatically judging step.

4. A particle agglutination judgment method for automatically classifying attributes of particle patterns of a sample into agglutination, non-agglutination, and other attributes, comprising the steps of:

a first step of providing a particle agglutination pattern judgment apparatus comprising reading means for optically measuring particle pattern images of the sample, and reading the particle pattern images to be able to execute pattern judgment processing; parameter calculation means for calculating predetermined parameters on the basis of the particle pattern images read by said reading means; judgment means for automatically judging an agglutination, non-agglutination, or unidentified attribute of each particle pattern of the sample on the basis of the parameters calculated by said parameter calculation means and a threshold value of the parameter; pattern image storage means for storing the particle pattern images read by said reading means and judgment results by said judgment means; first display means for displaying the automatic judgment results by said judgment means and for displaying the particle pattern images read by said reading means; input means for manually inputting data; and determination result storage means for storing visual judgment results input from said input means;

a second step of causing said reading means of said particle agglutination pattern judgment apparatus to optically measure the particle pattern images of the sample and to read the particle pattern images to be able to execute the pattern judgment processing;

a third step of causing said parameter calculation means of said particle agglutination pattern judgment apparatus to calculate the predetermined parameters on the basis of the particle pattern images read by said reading means;

a fourth step of visually observing the particle pattern images of the sample to visually judge an agglutination, non-agglutination, or unidentified attribute of each particle pattern of the sample and obtain visual judgment results, wherein said fourth step is executed for the particle pattern images of the sample, which is optically measured by said reading means;

a fifth step of inputting the visual judgment results of the fourth step to said particle agglutination pattern judgment apparatus using said input means of said particle agglutination pattern judgment apparatus, wherein the fifth step includes a step of inputting an agglutination, non-agglutination, or unidentified attribute of each visually judged particle pattern;

a sixth step of comparing the parameters calculated by said parameter calculation means and the visually judged input attributes to calculate the threshold value of the parameter which least conflicts with these data, wherein the sixth step includes the steps of:

storing the visual judgment results in said determination result storage means when the visual judgment results are input from said input means;

calculating the threshold value of the parameter on the basis of the parameters calculated by said parameter calculation means and the visual judgment results stored in said determination result storage means;

automatically judging the attributes of the particle patterns by said judgment means to obtain automatic judgment results;

displaying the automatic judgment results on said first display means;

determining whether or not there is a conflict between the automatic judgment results displayed on said first display means and the visual judgment results obtained by the fourth step;

inputting data for changing the threshold value by said input means when there is a conflict, wherein the inputting step includes a step of inputting storage correction instructions for correcting the visual judgment results stored in said determination result storage means;

a seventh step of correcting the visual judgment results stored in said determination result storage means according to the storage correction instructions;

an eighth step of recalculating the threshold value of a parameter on the basis of the corrected visual judgment results and the parameters calculated by said parameter calculation means;

a ninth step of causing said reading means of said particle agglutination pattern judgment apparatus to optically measure the particle pattern images of the sample and to read the particle pattern images to be able to execute the pattern judgment processing;

a tenth step of causing said parameter calculation means of said particle agglutination pattern judgment apparatus to obtain the predetermined parameters on the basis of the particle pattern images read by said reading means;

an eleventh step of automatically judging an agglutination, non-agglutination, or unidentified attribute of each particle pattern of the sample on the basis of the parameters calculated by said parameter calculation means by said judgment means of said particle agglutination pattern judgment apparatus;

a twelfth step of storing the judgment results, obtained when said judgment means automatically judges an agglutination, non-agglutination, or unidentified attribute of each particle pattern of the sample, in said pattern image storage means in correspondence with the particle pattern images;

a thirteenth step of displaying particle pattern images corresponding to the unidentified attribute of the automatic judgment results stored in said pattern image storage means by said display means;

a fourteenth step of visually observing the particle pattern images displayed on said display means to visually judge an agglutination, non-agglutination, or unidentified attribute of each particle pattern of the sample and obtain visual judgment results, wherein the fourteenth step is executed for the particle patterns which are judged to have the unidentified attribute in the eleventh step;

a fifteenth step of inputting an agglutination, non-agglutination, or unidentified attribute of each particle pattern which is judged to have the unidentified attribute in the eleventh step; and a sixteenth step of changing the attributes of the particle patterns which are judged to have the unidentified attribute in the eleventh step to the input attributes.

5. The method according to claim 4, further comprising a step of preparing rewriting means for changing a storage content of said pattern image storage means in said particle agglutination pattern judgment apparatus, and wherein the changing step includes a step of rewriting the automatic judgment results stored in said pattern image storage means with the input visual judgment results input by said input means.

6. The method according to claim 5, wherein the step of storing the judgment results in said pattern image storage means in correspondence with the particle patterns includes a step of storing the judgment result in correspondence with the particle pattern image only when an unidentified attribute is judged in the automatically judging step.

7. A particle agglutination judgment method for automatically classifying attributes of particle patterns of a sample into agglutination, non-agglutination, and other attributes, comprising the steps of:

a first step of providing a particle agglutination pattern judgment apparatus comprising reading means for optically measuring particle pattern images of the sample, and reading the particle pattern images to be able to execute pattern judgment processing; parameter calculation means for calculating predetermined parameters on the basis of the particle pattern images read by said reading means; judgment means for automatically judging an agglutination, non-agglutination, or unidentified attribute of each particle pattern of the sample on the basis of the parameters calculated by said parameter calculation means and a threshold value of the parameter; input means for manually inputting data; recording/reproducing means for recording/reproducing a plurality of reference sample pattern images used for setting the threshold value; and display means for displaying the plurality of reference sample pattern images reproduced by said recording/reproducing means;

a second step of sequentially displaying the plurality of reference sample pattern images reproduced by said recording/reproducing means on said display means;

a third step of executing visual judgments of the reference sample pattern images displayed on said display means;

a fourth step of inputting the visual judgement of an agglutination, non-agglutination, or unidentified attribute of each particle pattern of the reference sample pattern images;

a fifth step of reading the plurality of reference sample pattern images reproduced by said recording/reproducing means by said reading means;

a sixth step of calculating the predetermined parameters on the basis of the plurality of reference sample pattern images read by said reading means by said parameter calculation means;

a seventh step of comparing the parameters calculated by said parameter calculation means and the input attributes to obtain a threshold value of the parameter;

an eighth step of comparing the parameters calculated by said particle agglutination pattern judgment apparatus to optically measure the particle pattern images of the sample and to read the particle pattern images to be able to execute the pattern judgment processing;

a ninth step of causing said parameter calculation means of said particle agglutination pattern judgment apparatus to obtain the predetermined parameters on the basis of the particle pattern images read by said reading means;

a tenth step of automatically judging an agglutination, non-agglutination, or unidentified attribute of each particle pattern of the sample on the basis of the parameters calculated by said parameter calculation means and of the threshold value of the parameter obtained by said seventh step by said judgment means of said particle agglutination pattern judgment apparatus;

an eleventh step of visually observing the particle pattern images of the sample to visually judge an agglutination, non-agglutination, or unidentified attribute of each particle pattern of the sample and obtain visual judgment results, wherein the eleventh step is executed for the particle patterns which are judged to have the unidentified attribute in the tenth step;

a twelfth step of inputting the visual judgment results of the visually observing step to said particle agglutination pattern judgment apparatus using said input means of said particle agglutination pattern judgment apparatus; and a thirteenth step of changing the judgment results in the automatically judging step.

8. The method according to claim 7, wherein the eleventh step is further executed for the particle patterns which are judged to have the unidentified attribute in the tenth step, the twelfth step further includes a step of inputting an agglutination, non-agglutination, or unidentified attribute of each particle pattern which is judged to have the unidentified attribute in the tenth step, and the thirteenth step further includes a step of changing the attributes to the particle patterns which are judged to have the unidentified attribute in the tenth step to the input attributes.

9. The method according to claim 8, further comprising the steps of:

a fourteenth step of preparing second display means for displaying the particle pattern images read by said reading means and pattern image storage means for storing the particle pattern images read by said reading means and the judgment results by said judgment means in said particle agglutination pattern judgment apparatus;

a fifteenth step of storing the judgment results, obtained when said judgment means automatically judges an agglutination, non-agglutination, or unidentified attribute of each particle pattern of the sample, in said pattern image storage means in correspondence with the particle pattern images; and a sixteenth step of displaying particle pattern images corresponding to the unidentified attribute of the automatic judgment results stored in said pattern image storage means by said second display means, and wherein the eleventh step includes a step of visually observing the particle pattern images displayed on said second display means.

10. The method according to claim 9, further comprising a seventeenth step of preparing rewriting means for changing a storage content of said pattern image storage means in said particle agglutination pattern judgment apparatus, and wherein the thirteenth step includes a step of rewriting the automatic judgment results stored in said pattern image storage means with the input visual judgment results input by said input means.

11. The method according to claim 10, wherein the fifteenth step includes a step of storing the judgment result in correspondence with the particle pattern image only when an unidentified attribute is judged in the tenth step.

* * * * *